United States Patent
Lee et al.

(10) Patent No.: US 12,186,422 B2
(45) Date of Patent: Jan. 7, 2025

(54) COMPOSITION FOR INCREASING SILICONE DEPOSITION ON KERATIN FIBERS

(71) Applicant: L'OREAL, Paris (FR)

(72) Inventors: Isaac Eng Ting Lee, Kawasaki (JP); Stephanie Valentina, Yokohama (JP); Dhimoy Roy, Woodmead Johannesburg (ZA); Richard Ferguson, Tokyo (JP); Kazumitsu Kawakami, Westfield, NJ (US)

(73) Assignee: L'OREAL, Paris (FR)

( * ) Notice: Subject to any disclaimer, the term of this patent is extended or adjusted under 35 U.S.C. 154(b) by 694 days.

(21) Appl. No.: 17/285,628

(22) PCT Filed: Oct. 11, 2019

(86) PCT No.: PCT/JP2019/041237
§ 371 (c)(1),
(2) Date: Apr. 15, 2021

(87) PCT Pub. No.: WO2020/085268
PCT Pub. Date: Apr. 30, 2020

(65) Prior Publication Data
US 2021/0378943 A1    Dec. 9, 2021

(30) Foreign Application Priority Data
Oct. 23, 2018 (JP) .............................. 2018-199023

(51) Int. Cl.
| | | |
|---|---|---|
| *A61K 8/898* | (2006.01) | |
| *A61K 8/34* | (2006.01) | |
| *A61K 8/362* | (2006.01) | |
| *A61K 8/891* | (2006.01) | |
| *A61Q 5/12* | (2006.01) | |

(52) U.S. Cl.
CPC .............. *A61K 8/898* (2013.01); *A61K 8/34* (2013.01); *A61K 8/362* (2013.01); *A61K 8/891* (2013.01); *A61Q 5/12* (2013.01); *A61K 2800/5922* (2013.01); *A61K 2800/594* (2013.01)

(58) Field of Classification Search
CPC .......... A61K 8/898; A61K 8/34; A61K 8/362; A61K 8/891; A61K 2800/5922; A61K 2800/594; A61Q 5/12
See application file for complete search history.

(56) References Cited

U.S. PATENT DOCUMENTS

| | | |
|---|---|---|
| 2017/0151142 A1 | 6/2017 | Scheunemann et al. |
| 2018/0055751 A1* | 3/2018 | Gevgilili ................ A61K 8/362 |

FOREIGN PATENT DOCUMENTS

| | | |
|---|---|---|
| EP | 1649847 A1 | 4/2006 |
| JP | 2007-008867 A | 1/2007 |
| JP | 2007-161605 A | 6/2007 |
| JP | 2008-297245 A | 12/2008 |
| JP | 2009-007283 A | 1/2009 |
| JP | 2015-117223 A | 6/2015 |
| WO | 2014/104340 A1 | 7/2014 |

OTHER PUBLICATIONS

International Search Report and Written Opinion for counterpart Application No. PCT/JP2019/041237, dated Jan. 29, 2020.
Mintel: "Conditioner," Anonymous, XP055658847, Database Accession No. 5882741, Aug. 7, 2018.
Translation of Japanese Office Action for counterpart Application No. 2021-520626, dated May 16, 2022.
Machine Translation of Search Report for Chinese Application No. 201980069524.7, dated Sep. 28, 2022.
Sun, Jia-ying et al., "Study on rinse-off conditioners prepared by the modified amino silicone oil," Applied Chemical Industry, vol. 46, No. 10, Oct. 2017, pp. 1942-1945 (English Abstract).

* cited by examiner

*Primary Examiner* — Snigdha Maewall
(74) *Attorney, Agent, or Firm* — THE MARBURY LAW GROUP, PLLC

(57) ABSTRACT

The present invention relates to a composition for treating keratin fibers, preferably hair, comprising (a) tartaric acid, (b) at least one aromatic alcohol, (c) at least one organopolysiloxane selected from polydialkylsiloxane, polydiarylsiloxane, and polyalkylarylsiloxane, and (d) at least one amino-modified silicone.

17 Claims, No Drawings

COMPOSITION FOR INCREASING SILICONE DEPOSITION ON KERATIN FIBERS

CROSS REFERENCE TO RELATED APPLICATION

This is a national stage application of PCT/JP2019/041237, filed internationally on Oct. 11, 2019, which claims priority to Japanese Application No. 2018-199023, filed on Oct. 23, 2018, both of which are incorporated by reference herein in their entireties.

TECHNICAL FIELD

The present invention relates to a composition for increasing silicone deposition on keratin fibers, in particular hair, comprising tartaric acid, at least one aromatic alcohol, at least one organopolysiloxane selected from polydialkylsiloxane, polydiarylsiloxane, and polyalkylarylsiloxane, and at least one amino-modified silicone.

BACKGROUND ART

In the field of hair cosmetics, a hair conditioning effect is a very important property. It is well known that silicones impart a conditioning effect on hair. To date, some prior art documents relating to rinse-off type hair care cosmetic products comprising silicones have been published.

WO 2014/104340 discloses a rinse-off type hair cosmetic composition including: component (A), namely a cationic polymer having a cationic charge density in the range of 4 meq/g to 10 meq/g inclusive; component (B), namely a fatty acid; component (C), namely a cationic surface active agent; component (D), namely a silicone; and component (E), namely either an organic acid or an inorganic acid, wherein the mass ratio ((A)/(B)) of component (A) to component (B) is in the range of 0.1 to 9 inclusive, component (A) and component (B) form a water-insoluble composite, and the pH (at 25° C.) of the composition when diluted 20-fold is in the range of 2 to 5 inclusive.

However, there is still a demand for hair care cosmetic products with improved cosmetic effects. In particular, there is a demand for hair care cosmetic products for increasing silicone deposition on keratin fibers, such as hair, to ensure improved cosmetic effects, such as smoothing keratin fibers, as well as providing the long lastingness of the cosmetic effects.

DISCLOSURE OF INVENTION

An objective of the present invention is to provide a composition for increasing silicone deposition on keratin fibers, such as hair, while maintaining the deposition on keratin fibers over a long term. The composition according to the present invention can achieve improved cosmetic effects, such as smoothing keratin fibers, such as hair, in consideration of an increased amount of silicone deposition on keratin fibers as well as long-lastingness of the cosmetic effects.

The above objective of the present invention can be achieved by a composition for treating keratin fibers, preferably hair, comprising:
(a) tartaric acid in an amount of 0.3% by weight or more relative to the total amount of the composition,
(b) at least one aromatic alcohol,
(c) at least one organopolysiloxane selected from polydialkylsiloxane, polydiarylsiloxane, and polyalkylarylsiloxane, and
(d) at least one amino-modified silicone.

The aromatic alcohol may be represented by general formula (I):

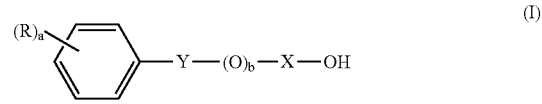

wherein,
a indicates an integer of 0 to 5, preferably 0 to 2, and more preferably 0 or 1;
b indicates an integer of 0 or 1;
R indicates H, a halogen, a $C_1$ to $C_6$ alkyl, a $C_1$ to $C_6$ alkoxy, or a $C_1$ to $C_6$ alkenyl group;
X indicates a $C_1$ to $C_4$ alkylene or a $C_1$ to $C_4$ alkynylene group; and
Y indicates a single bond, a $C_1$ to $C_4$ alkylene, or a $C_1$ to $C_4$ alkynylene group.

Preferably, in general formula (I),
a indicates an integer of 0 or 1;
b indicates an integer of 0 or 1;
R indicates H, a halogen, or a $C_1$ to $C_6$ alkyl group;
X indicates a $C_1$ to $C_4$ alkylene group; and
Y indicates single bond or a $C_1$ to $C_4$ alkylene group.

More preferably, in general formula (I),
a is 0;
b is 1;
X indicates a $C_1$ to $C_4$ alkylene group; and
Y indicates a single bond.

In one preferred embodiment of the present invention, the aromatic alcohol is phenoxyethanol.

The organopolysiloxane may be selected from polydialkylsiloxane, such as polydimethylsiloxane.

The tartaric acid may be present in a content ranging from 0.3% to 20% by weight, preferably from 0.4% to 15% by weight, and more preferably from 0.5% to 10% by weight, relative to the total weight of the composition.

The aromatic alcohol may be present in a content ranging from 0.05% to 10% by weight, preferably from 0.1% to 5% by weight, and more preferably from 0.2% to 3% by weight, relative to the total weight of the composition.

The organopolysiloxane may be present in a content ranging from 0.1% to 30% by weight, preferably from 1% to 20% by weight, and more preferably from 2% to 15% by weight, relative to the total weight of the composition.

The amino-modified silicone may be present in a content ranging from 0.1% to 20% by weight, preferably from 0.5% to 15% by weight, and more preferably from 1% to 10% by weight, relative to the total weight of the composition.

The composition according to the present invention may further comprise at least one surfactant selected from cationic, anionic, nonionic, and amphoteric surfactants.

The composition according to the present invention may further comprise at least one oil.

In one embodiment of the present invention, the composition according to the present invention is a rinse-off type cosmetic composition.

The present invention also relates to a cosmetic process for caring for or conditioning keratin fibers, preferably hair, comprising the step of applying onto the keratin fibers the composition according to the present invention.

BEST MODE FOR CARRYING OUT THE INVENTION

After diligent research, the inventors have surprisingly found out that a combination of the components (a) to (d) above can provide an increased amount of silicone deposition and its long-lastingness on the surface of keratin fibers, such as hair, and thus they have completed the present invention.

Thus, the composition for treating keratin fibers, preferably hair, according to the present invention comprises:
(a) tartaric acid in an amount of 0.3% by weight or more relative to the total amount of the composition,
(b) at least one aromatic alcohol,
(c) at least one organopolysiloxane selected from polydialkylsiloxane, polydiarylsiloxane, and polyalkylarylsiloxane, and
(d) at least one amino-modified silicone.

The "keratin fibers" here mean fibers which include at least one keratin substance. It is preferable that at least a part of the surface of the keratin fibers be formed by keratin substances. Examples of keratin fibers include hair, eyebrows, eyelashes, and the like. It is preferable that the present invention be used for treating hair.

Especially, the composition according to the present invention has a superior effect of increasing the amount of silicone deposition on keratin fibers, such as hair. Therefore, the composition according to the present invention can provide improved cosmetic effects, such as smoothness, which can be produced from silicone deposition on the surface of keratin fibers. Furthermore, the composition according to the present invention can impart long-lastingness of the cosmetic effects.

Hereafter, the composition according to the present invention will be described in a detailed manner.
[Composition]

The composition for treating keratin fibers, preferably hair, according to the present invention comprises (a) tartaric acid in an amount of 0.3% by weight or more relative to the total amount of the composition, (b) at least one aromatic alcohol, (c) at least one organopolysiloxane selected from polydialkylsiloxane, polydiarylsiloxane, and polyalkylarylsiloxane, and
(d) at least one amino-modified silicone.
(Tartaric Acid)

The composition according to the present invention comprises (a) tartaric acid. The (a) tartaric acid is included in the composition in an amount of 0.3% by weight or more relative to the total amount of the composition.

Tartaric acid can be represented by the general formula below.

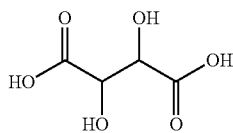

The inventors surprisingly found out that the use of the combination of tartaric acid in an amount of 0.3% by weight or more relative to the total amount of the composition and an aromatic alcohol with the silicones including the organopolysiloxane and the amino-modified silicone can provide a superior hair smoothing effect as well as long-lastingness of such effect. Therefore, the present invention can achieve an attractive appearance and enhanced manageability of the hair over a long term.

The (a) tartaric acid may be present in a content of 0.3% by weight or more, preferably 0.4% by weight or more, and more preferably 0.5% by weight or more, relative to the total weight of the composition. The tartaric acid may be present in a content of 20% by weight or less, preferably 15% by weight or less, more preferably 10% by weight or less, and even more preferably 5% by weight or less, relative to the total weight of the composition.

The (a) tartaric acid may be present in a content ranging from 0.3% to 20% by weight, preferably from 0.4% to 15% by weight, and more preferably from 0.5% to 10% by weight, relative to the total weight of the composition. In other embodiments, the tartaric acid may be present in a content ranging from 0.3% to 15% by weight, preferably from 0.4% to 10% by weight, and more preferably from 0.5% to 5% by weight, relative to the total weight of the composition.
(Aromatic Alcohol)

The composition according to the present invention comprises (b) at least one aromatic alcohol. Two or more (b) aromatic alcohols may be used in combination. Thus, a single type of aromatic alcohol or a combination of different types of aromatic alcohols may be used.

The term "aromatic alcohol" used herein means any compound comprising at least one aromatic ring and at least one alcohol functional group, i.e. —OH group, directly linked to the aromatic ring or linked to at least one substituent on the ring.

The (b) aromatic alcohol may be a mono-alcohol having one —OH group or a polyol having two or more —OH groups such as di-alcohol. Preferably, the aromatic alcohol is a mono-alcohol.

The (b) aromatic alcohol preferably includes one or more benzene ring(s), naphthalene ring(s), or furan ring(s). More preferably, the aromatic alcohol includes one or more benzene rings. In particular, the aromatic alcohol may include one benzene ring.

In one preferable embodiment of the present invention, the (b) aromatic alcohol includes one benzene ring and one —OH group linked to a substituent on the ring.

The (b) aromatic alcohol can be a primary alcohol, a secondary alcohol, or a tertiary alcohol. Preferentially, the aromatic alcohol is a primary alcohol.

In one preferred embodiment of the present invention, the aromatic alcohol can be represented by the following general formula (I):

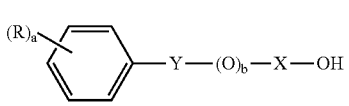

wherein,
a indicates an integer of 0 to 5, preferably 0 to 2, and more preferably 0 or 1;
b indicates an integer of 0 or 1;
R indicates H, a halogen, a $C_1$ to $C_6$ alkyl, a $C_1$ to $C_6$ alkoxy, or a $C_1$ to $C_6$ alkenyl group;
X indicates a $C_1$ to $C_4$ alkylene or a $C_1$ to $C_4$ alkynylene group; and Y indicates a single bond, a $C_1$ to $C_4$ alkylene, or a $C_1$ to $C_4$ alkynylene group.

Each of said alkyl, alkoxy, alkenyl, alkylene, and alkynylene groups can be linear or branched and can be substituted with one or more substituents selected from a halogen, amine group (—$NH_2$), and oxo group (=O).

The halogen can be selected from F, Cl, Br, and I, and preferably the halogen is Cl.

According to one preferred embodiment of the present invention, in general formula (I),
a indicates an integer of 0 or 1;
b indicates an integer of 0 or 1;
R indicates H, a halogen, or a $C_1$ to $C_6$ alkyl group;
X indicates a $C_1$ to $C_4$ alkylene group; and
Y indicates a single bond or a $C_1$ to $C_4$ alkylene group.

According to one particularly preferred embodiment of the present invention, in general formula (I),
a is 0;
b is 1;
X indicates a $C_1$ to $C_4$ alkylene group; and
Y indicates a single bond.

In another embodiment of the present invention, the (b) aromatic alcohol used herein can be selected from benzyl alcohol, benzyl glycol, phenoxyethanol, dichlorobenzyl alcohol, methylphenylbutanol, phenoxyisopropanol, 1-phenyl-1-propanol, 1-phenyl-2-propanol, 2-phenyl-1-propanol, 2-phenyl-2-propanol, 3-phenyl-1-propanol, 1-phenylethyl alcohol, 2-phenylethyl alcohol, benzyloxy ethanol, cinnamyl alcohol, 4-methoxybenzyl alcohol, 4-methylbenzyl alcohol, and mixtures thereof. Particularly preferably, the aromatic alcohol is phenoxyethanol.

The (b) aromatic alcohol may be present in a content of 0.05% by weight or more, preferably 0.1% by weight or more, more preferably 0.2% by weight or more, and even more preferably 0.5% by weight or more, relative to the total weight of the composition. The aromatic alcohol may be present in a content of 10% by weight or less, preferably 5% by weight or less, and more preferably 3% by weight or less, relative to the total weight of the composition.

The (b) aromatic alcohol may be present in a content ranging from 0.05% to 10% by weight, preferably from 0.1% to 5% by weight, and more preferably from 0.2% to 3% by weight, relative to the total weight of the composition. In other preferable embodiments, the aromatic alcohol may be present in a content ranging from 0.1% to 10% by weight, preferably from 0.2% to 5% by weight, and more preferably from 0.5% to 3% by weight, relative to the total weight of the composition.

(Silicone)

The composition according to the present invention comprises at least two types of silicones, i.e. (c) at least one organopolysiloxane selected from polydialkylsiloxane, polydiarylsiloxane, and polyalkylarylsiloxane, and (d) at least one amino-modified silicone. Therefore, the silicones included in the composition include a combination of the (c) organopolysiloxane and the (d) amino-modified silicone.

Two or more (c) organopolysiloxanes selected from polydialkylsiloxane, polydiarylsiloxane, and polyalkylarylsiloxane may be used in combination. Thus, a single type of organopolysiloxane or a combination of different types of organopolysiloxanes may be used. Also, two or more (d) amino-modified silicones may be used in combination. Thus, a single type of amino-modified silicone or a combination of different types of amino-modified silicones may be used.

In the context of the present invention, the term "silicone" used herein is understood to mean, in conformity with the generally accepted definition, all organosilicone polymers or oligomers having a linear or cyclic, branched or crosslinked structure, of variable molecular weight, obtained by polymerization and/or polycondensation of appropriately functionalized silanes, and comprising in essence a repetition of main units in which the silicon atoms are joined to one another by oxygen atoms (siloxane link ≡Si—O—Si≡), optionally substituted hydrocarbon radicals being linked directly via a carbon atom to the said silicon atoms. The most common hydrocarbon radicals are alkyl radicals, in particular $C_1$-$C_{10}$ alkyl radicals and especially methyl, fluoroalkyl radicals, and aryl radicals and especially phenyl.

The (c) organopolysiloxane(s) and the (d) amino-modified silicone(s) used in the present invention can be volatile silicone, non-volatile silicone, or combinations thereof. Preferably, the (c) organopolysiloxane(s) and the (d) amino-modified silicone(s) are non-volatile silicones.

In the interest of simplicity, the kinetic viscosity of the silicones of the (c) organopolysiloxane(s) and the (d) amino-modified silicone(s) is denoted "viscosity". The viscosity of the silicones at 25° C. is not particularly limited, but in general can be 5 $mm^2/s$ to 30,000,000 $mm^2/s$, preferably from 100 $mm^2/s$ to 20,000,000 $mm^2/s$. The viscosity of the silicones according to the present invention is preferably measured using a Poiseuille rheometer, at a temperature of 25° C., according to standard ASTM-D445-97. When the silicones are used as a mixture in a solvent or in the form of an emulsion, the viscosity of the silicones alone is measured, independently of the mixture solvent.

The weight-average molecular weights (Mw) of the silicones of the (c) organopolysiloxane(s) and the (d) amino-modified silicone(s) are not particularly limited, but in general can range from 10,000 to 4,000,000, preferably from 50,000 to 3,000,000, and more preferably from 100,000 to 2,000,000. The weight-average molecular weights (Mw) of the silicones are measured by gel permeation chromatography (GPC) at ambient temperature, as polystyrene equivalents. The columns used are micro styragel columns. The eluent is THF and the flow rate is 1 ml/minute. 200 μl of a solution containing 0.5% by weight of the silicones in THF are injected. Detection is performed by refractometry and UV-metry.

The (c) organopolysiloxane(s) is (are) selected from polydialkylsiloxanes, polydiarylsiloxanes, and polyalkylarylsiloxanes. Preferably, the organopolysiloxane(s) is (are) selected from polydialkylsiloxanes, such as polydimethylsiloxanes (PDMS).

The (c) organopolysiloxane(s) are defined in greater detail in the book by Walter Noll, "Chemistry and Technology of Silicones" (1968), Academic Press. Among polydialkylsiloxanes, mention may be made of linear polydimethylsiloxanes with trimethylsilyl end groups, and polydimethylsiloxanes with hydroxydimethylsilyl end groups, for instance. Among polyalkylarylsiloxanes, mention may be made of linear and branched polydimethylmethylphenylsiloxanes and polydimethyldiphenylsiloxanes, for instance.

According to one embodiment, the (c) organopolysiloxane(s) may be chosen from non-volatile polydialkylsiloxanes, for example, polydimethylsiloxanes with trimethylsilyl end groups known under the trade name dimethicones.

Non-limiting examples of commercial products corresponding to such polydialkylsiloxanes include BY22-029 (product of Dow Corning Toray, Co., Ltd.; nonionic emulsion of dimethicone oil), BY22-060 (product of Dow Corning Toray, Co., Ltd.; cationic emulsion containing a solution obtained by diluting highly polymerized dimethicone with a low viscosity silicone), BY22-019 (product of Dow Corning Toray, Co., Ltd.; nonionic and cationic emulsion containing a solution obtained by diluting highly polymerized dimethicone with cyclic silicone), BY22-020 (product of Dow Corning Toray, Co., Ltd.; cationic emulsion containing a solution obtained by diluting a highly polymerized dimethicone with light liquid isoparaffin), KM902 (product of Shin-Etsu Chemical Co., Ltd.; nonionic emulsion of highly polymerized dimethicone), KM903 (product of Shin-Etsu Chemical Co., Ltd.; cationic emulsion containing a solution obtained by diluting a highly polymerized dimethicone with a low viscosity silicone), X-52-2127 (product of Shin-Etsu Chemical Co., Ltd.; cationic emulsion containing a solution obtained by diluting a highly polymerized dimethicone with low viscosity silicone), X-52-2162 (product of Shin-Etsu Chemical Co., Ltd.; nonionic emulsion containing a solution obtained by diluting a highly polymerized dimethicone with low viscosity silicone), EMU101 (product of Momentive Performance Materials, Inc.; nonionic emulsion containing a solution obtained by diluting highly polymerized dimethicone with low viscosity silicone), XS65-B3803 (product of Momentive Performance Materials, Inc.; nonionic emulsion containing a solution obtained by diluting highly polymerized dimethicone with low viscosity silicone), and DC 7-3100 (product of Dow Corning Toray Silicone, Co., Ltd.).

According to the present invention, the (d) amino-modified silicone, or amino silicone, denotes any silicone comprising at least one primary, secondary or tertiary amine or at least one quaternary ammonium, and more particularly at least one primary amine.

The (d) amino-modified silicones used in the present invention can be chosen from the silicones of formula (II) below:

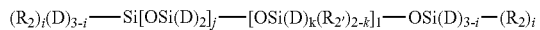

(II)

in which,

D is a hydrogen atom, or a phenyl, hydroxyl (—OH), or $C_1$-$C_8$ alkyl, and preferably methyl, or $C_1$-$C_8$ alkoxy, preferably methoxy, radical, i denotes the number 0 or an integer from 1 to 3, and preferably 0, k denotes 0 or 1, and in particular 1, j and l are numbers such that the sum (j+l) can range especially from 1 to 2000 and in particular from 50 to 150, it being possible for j to denote a number from 0 to 1999 and in particular from 49 to 149, and for l to denote a number from 1 to 2000 and in particular from 1 to 10;

$R_2$ is a monovalent radical of formula —$C_qH_{2q}L$ in which q is a number from 2 to 8, it being possible for one or more hydrogen atoms to be substituted with a hydroxyl group, and L is an optionally quaternized amino group chosen from the groups:

N($R_3$)—$CH_2$—$CH_2$—N($R'_3$)$_2$;
N($R_3$)$_2$;
N$^+$(R3)$_3$Q$^-$;
N$^+$($R_3$)(H)$_2$Q$^-$;
N$^+$($R_3$)$_2$HQ$^-$;
—N($R_3$)—$CH_2$—$CH_2$—N$^+$($R'_3$)(H)$_2$Q$^-$, in which $R_3$ and $R'_3$ can denote a hydrogen atom, a phenyl, a benzyl, or a monovalent saturated hydrocarbon-based radical, for example a $C_1$-$C_{20}$ alkyl radical, and Q and Q$^-$ represent an anion such as, for example, fluoride, chloride, bromide or iodide.

In particular, the (d) amino-modified silicones corresponding to the definition of formula (II) can be chosen from the compounds corresponding to formula (III) below:

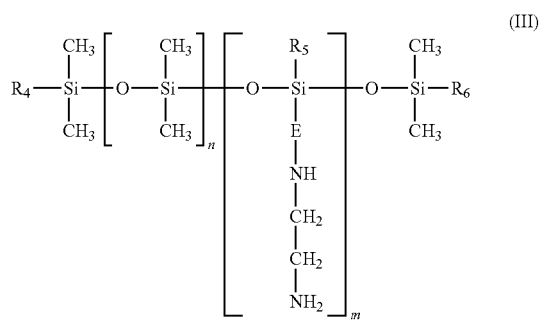

(III)

in which $R_4$, $R_5$ and $R_6$, which may be identical or different, denote a $C_1$-$C_4$ alkyl radical, preferably $CH_3$; a $C_1$-$C_4$ alkoxy radical, preferably methoxy; or OH; E represents a linear or branched, $C_3$-$C_8$ and preferably $C_3$-$C_6$ alkylene radical; m and n are integers dependent on the molecular weight and the sum of which is between 1 and 2000.

According to a first possibility, $R_4$, $R_5$ and $R_6$, which may be identical or different, represent a $C_1$-$C_4$ alkyl radical, preferably methyl, or a hydroxyl radical, E represents a $C_1$-$C_8$ and preferably $C_3$-$C_4$ alkylene radical, and m and n are such that the weight-average molecular weight of the compound is between 5,000 and 500,000 approximately. The compounds of this type are called "aminodimethicones" in the CTFA dictionary.

According to a second possibility, $R_4$, $R_5$ and $R_6$, which may be identical or different, represent a $C_1$-$C_4$ alkoxy or hydroxyl radical, at least one of the radicals $R_4$ or $R_5$ is an alkoxy radical and E represents a $C_3$ alkylene radical. The hydroxy/alkoxy molar ratio is preferably between 0.2/1 and 0.4/1 and advantageously equals 0.3/1. Moreover, m and n are such that the weight-average molecular weight of the compound is between 2,000 and 1,000,000. More particularly, n is between 0 and 999 and m is between 1 and 1,000, the sum of n and m being between 1 and 1,000. In this category of compounds, mention may be made, inter alia, of the product Belsil® ADM 652 sold by Wacker.

According to a third possibility, $R_4$ or $R_6$, which are different, represents a $C_1$-$C_4$ alkoxy or hydroxyl radical, at least one of the radicals $R_5$ or $R_6$ is an alkoxy radical, $R_5$ represents a methyl radical and E represents a $C_3$ alkylene radical. The hydroxy/alkoxy molar ratio is preferably between 1/0.8 and 1/1.1, and advantageously is equal to 1/0.95. Moreover, m and n are such that the weight-average molecular weight of the compound is between 2,000 and 200,000. More particularly, n is between 0 and 999 and m is between 1 and 1,000, the sum of n and m being between 1 and 1,000. More particularly, mention may be made of the product Fluid WR® 1300 sold by Wacker, and the product Xiameter® MEM-8299 Emulsion sold by Dow Corning.

The (d) amino-modified silicones used in the composition in accordance with the invention preferably have general formula (IV) below:

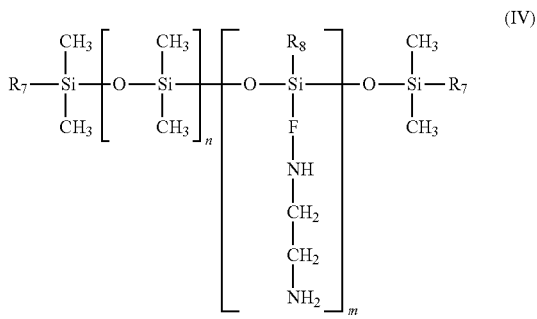

in which:
F denotes a $C_2$-$C_8$ and preferably $C_2$-$C_6$, better still $C_3$, linear or branched alkylene radical;
$R_7$ and $R_8$ denote, independently of one another, a $C_1$-$C_4$ alkyl, preferably methyl, radical or a $C_1$-$C_4$ alkoxy, preferably methoxy, radical or a hydroxyl radical, m and n are numbers such that the weight-average molecular weight (Mw) is greater than or equal to 75,000. Preferably, the radicals $R_7$ are identical and denote a hydroxyl radical.

Preferably, the viscosity of the (d) amino-modified silicone according to the invention is greater than 25,000 mm²/s measured at 25° C. More preferentially, the viscosity of the amino-modified silicone is between 30,000 and 200,000 mm²/s at 25° C., even more preferentially between 50,000 and 150,000 mm²/s, measured at 25° C., and even better still from 70,000 to 120,000 mm²/s.

Preferably, the cationic charge of the (d) amino-modified silicone according to the invention is less than or equal to 0.5 meq/g, preferably ranging from 0.01 to 0.1 meq/g and better still from 0.03 to 0.06 meq/g.

Preferably, the (d) amino-modified silicone according to the invention has a weight-average molecular weight (Mw) ranging from 10,000 to 100,000 and even more preferentially ranging from 20,000 to 50,000.

A particularly preferred amino silicone corresponding to formula (IV) is, for example, Dow Corning 2-8299 Cationic Emulsion from the company Dow Corning.

A product corresponding to the definition of formula (II) is in particular the polymer called "trimethylsilylamodimethicone" in the CTFA dictionary, corresponding to formula (V) below:

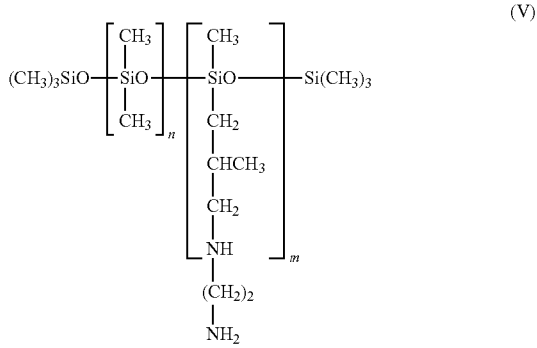

in which n and m have the meanings given above in accordance with formula (III).

Such compounds are described, for example, in EP 95238; a compound of formula (V) is, for example, sold under the name Q2-8220 by the company OSI.

Other amino silicones according to the invention are quaternized amino silicones, and in particular:
the compounds corresponding to formula (VI) below:

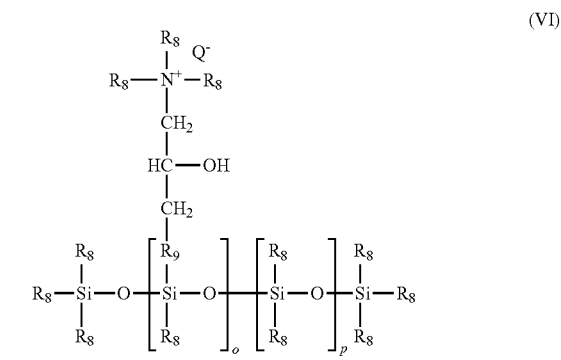

in which,
$R_8$ represents a $C_1$-$C_{18}$ alkyl radical, for example methyl;
$R_9$ represents a divalent hydrocarbon-based radical, in particular a $C_1$-$C_{18}$ alkylene radical;
$Q^-$ is an anion, in particular chloride;
o represents a mean statistical value from 2 to 20 and in particular from 2 to 8;
p represents a mean statistical value from 20 to 200 and in particular from 20 to 50.

Such compounds are described more particularly in the patent, U.S. Pat. No. 4,185,087. A compound falling within this class is the product sold by the company Union Carbide under the name Ucar Silicone ALE 56;
the quaternary ammonium silicones of formula (VII):

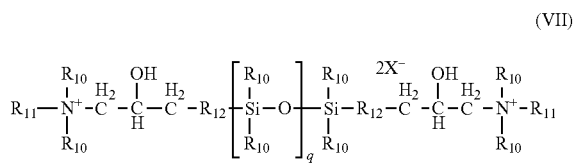

in which:
$R_{10}$, which may be identical or different, represent a monovalent hydrocarbon-based radical containing from 1 to 8 carbon atoms, and in particular a $C_1$-$C_8$ alkyl radical, for example methyl;
$R_{12}$ represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;
$R_{11}$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_{12}$—$NHCOR_{10}$;
$X^-$ is an anion such as a halide ion, especially chloride, or an organic acid salt (acetate, etc.);
r represents a mean statistical value from 2 to 200 and in particular from 5 to 100.

These silicones are, for example, described in the application, EP-A-0530974;

the amino-modified silicones of formula (VIII):

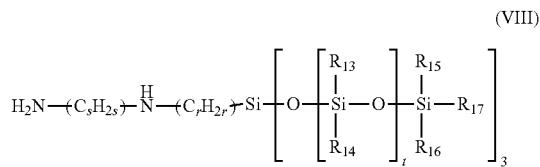

(VIII)

in which:
$R_{13}$, $R_{14}$, $R_{15}$ and $R_{16}$, which may be identical or different, denote a $C_1$-$C_4$ alkyl radical or a phenyl group, $R_{17}$ denotes a $C_1$-$C_4$ alkyl radical or a hydroxyl group, r is an integer ranging from 1 to 5, s is an integer ranging from 1 to 5, and in which t is selected such that the amine number is between 0.01 and 1 meq/g.

Preferably, the (d) amino-modified silicones of the invention are non-quaternized, i.e. they do not comprise a nitrogen atom with a permanent charge.

Preferably, the (d) amino-modified silicone of the present invention is amodimethicone such as the amodimethicone sold under the name KF 8020 from the supplier Shin Etsu, or the tradename SILSOFT 253 from the supplier MOMENTIVE PERFORMANCE MATERIALS. Another preferred amino-modified silicone is an amodimethicone of formula (F) sold under the tradename XIAMETER® MEM-8299 Cationic Emulsion by Dow Corning. Another preferred amino-modified silicone is an amodimethicone sold under the tradename Dow Corning® 969 EMULSION by Dow Corning.

Another preferred amino-modified silicone that may be used in the composition of the present invention is aminopropyl dimethicone, for example, aminopropyl dimethicone sold under the name KF-8015 from Shin Etsu.

In other embodiments, the amino-modified silicone of the present invention is chosen from bis-cetearyl amodimethicone (sold under the name SILSOFT AX by Momentive).

Another preferred aminosilicone that may be used in the composition of the present invention is aminopropyl dimethicone, for example, aminopropyl dimethicone sold under the name KF-8015 from Shin Etsu.

The (d) amino-modified silicone(s) which, is(are) particularly preferred in accordance with the invention is(are) polysiloxane(s) comprising amino groups, such as amodimethicones or trimethylsilylamodimethicones, and in particular the compounds of formulae (III), (IV) and (V).

The silicones of the (c) organopolysiloxane(s) and the (d) amino-modified silicone(s) can be used as they are or in the form of solutions in organic solvents or else in the form of emulsions or microemulsions. Preferably, the silicone is in the form of an aqueous emulsion. The term "aqueous emulsion" is intended to mean an emulsion of oil-in-water type in which the silicone copolymer is dispersed in the form of particles or droplets in the aqueous phase forming the continuous phase of the emulsion. This silicone emulsion can have a silicone droplet or particle size ranging from 10 nm to 50 μm, and preferably from 0.3 μm to 20 μm. The particle size is measured by laser particle sizing. This emulsion can be stabilized with a customary emulsifying system. The emulsifying system comprises surfactants that are normally used in silicone emulsions. These surfactants may be non-ionic, cationic, anionic or amphoteric surfactants or mixtures thereof.

The (c) organopolysiloxane(s) selected from polydialkylsiloxane, polydiarylsiloxane, and polyalkylarylsiloxane may be present in a content of 0.1% by weight or more, preferably 0.5% by weight or more, more preferably 1% by weight or more, and even more preferably 2% by weight or more, relative to the total weight of the composition. The (c) organopolysiloxane(s) may be present in a content of 30% by weight or less, preferably 20% by weight or less, more preferably 15% by weight or less, and even more preferably 10% by weight or less, relative to the total weight of the composition.

The (c) organopolysiloxane(s) selected from polydialkylsiloxane, polydiarylsiloxane, and polyalkylarylsiloxane may be present in a content ranging from 0.1% to 30% by weight, preferably from 0.5% to 20% by weight, more preferably from 1% to 15% by weight, and even more preferably from 2% to 10% by weight, relative to the total weight of the composition.

The (d) amino-modified silicone(s) may be present in a content of 0.1% by weight or more, preferably 0.5% by weight or more, and even more preferably 1% by weight or more, relative to the total weight of the composition. The (d) amino-modified silicone(s) may be present in a content of 20% by weight or less, preferably 15% by weight or less, and even more preferably 10% by weight or less, relative to the total weight of the composition.

The (d) amino-modified silicone(s) may be present in a content ranging from 0.1% to 20% by weight, preferably from 0.5% to 15% by weight, and even more preferably from 1% to 10% by weight, relative to the total weight of the composition.

In one certain embodiment of the present invention, the (c) organopolysiloxane(s) selected from polydialkylsiloxane, polydiarylsiloxane, and polyalkylarylsiloxane may be present in a content greater than that of the (d) amino-modified silicone(s) in the composition according to the present invention.

(Other Ingredients)
Surfactants

The composition according to the present invention may preferably include at least one surfactant. The surfactants used in the present invention include cationic, anionic, nonionic, and amphoteric surfactants.

As the nonionic surfactants, mention may be made of:
polyethoxylated fatty alcohols or polyglycerolated fatty alcohols, such as the adducts of ethylene oxide with lauryl alcohol, especially those containing from 9 to 50 oxyethylene units (Laureth-9 to Laureth-50, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 2 to 20 oxyethylene units (Steareth-2 to Steareth-20, as the CTFA names); the adducts of ethylene oxide with oleyl alcohol, especially those containing from 10 to 30 oxyethylene units (Oleth-10 to Oleth-30, for example Oleth-20, as the CTFA names); and mixtures thereof esters of sugar and of a $C_8$-$C_{24}$ fatty acid and their oxyalkylenated derivatives, such as polyethoxylated sorbitol esters of $C_8$-$C_{24}$ fatty acids, in particular Polysorbate 80, such as the product marketed under the name "TWEEN 80" by Croda and Polysorbate 20, such as the product marketed under the name "TWEEN 20" by Croda; ethers of a sugar and of $C_8$-$C_{24}$ fatty alcohols, such as caprylyl/capryl glucoside such as the product marketed under the name "ORAMIX CG 110" by SEPPIC;

esters of fatty acids, especially of $C_8$-$C_{24}$ and preferably of $C_{16}$-$C_{22}$, and of polyol, especially of glycerol or sorbitol, such as glyceryl stearate, sold, for example, under the name Tegin M® by the company Goldschmidt, polyglyceryl diisostearate, polyglyceryl isostearate, polyglyceryl monostearate, diglyceryl tetraisostearate, polyethylene glycol diisostearate, polyglyceryl-10 pentastearate, glyceryl monooleate, glyceryl laurate, such as the product Imwitor 312@ by the company Hills, diethylene glycol (di)laurate, decaglyceryl pentaoleate, decaglyceryl pentadiisostearate, glyceryl caprate/caprylate, polyglyceryl-2 (iso)stearate and (poly)ricinoleate;

oxyalkylenated alcohols, in particular oxyethylenated and/or oxypropylenated alcohols, which may comprise from 1 to 15 oxyethylene and/or oxypropylene units, in particular ethoxylated $C_8$-$C_{24}$ and preferably $C_{12}$-$C_{18}$ fatty alcohols such as stearyl alcohol ethoxylated with 2 oxyethylene units (CTFA name: Steareth-2 such as Brij 72 sold by the company Uniqema), or oxyethylenated oleyl alcohol.

As the anionic surfactants, mention may be made of:

salts of $C_{16}$-$C_{30}$ fatty acids, especially amine salts, such as triethanolamine stearate or 2-amino-2-methylpropane-1,3-diol stearate;

polyoxyethylenated fatty acid salts, especially aminated salts or salts of alkali metals, and mixtures thereof;

phosphoric esters and salts thereof, such as DEA oleth-10 phosphate (Crodafos N ION from the company Croda) or monopotassium monocetyl phosphate (Amphisol K from Givaudan or Arlatone MAP 160K from the company Uniqema);

sulfosuccinates such as Disodium PEG-5 citrate lauryl sulfo succinate and Disodium ricinoleamido MEA sulfo succinate;

alkyl ether sulfates such as sodium lauryl ether sulfate;

isethionates;

acylglutamates such as Disodium hydrogenated tallow glutamate (Amisoft HS-21 R®) sold by the company Ajinomoto), and mixtures thereof.

As the cationic surfactants, mention may be made of:

alkylimidazolidiniums such as isostearylethylimidonium ethosulfate, ammonium salts such as ($C_{12}$-$C_{30}$ alkyl)tri($C_1$-$C_4$ alkyl) ammonium halides, for instance N,N,N-trimethyl-1-docosanaminium chloride or behentrimonium chloride, and Quaternium-87.

As the amphoteric surfactants, mention may be made of N-acylamino acids such as N-alkyl aminoacetates and disodium cocoamphodi acetate, and amine oxides such as stearamine oxide and lauramine oxide.

The surfactant(s) may be present in a content ranging from 0.01% to 30% by weight, preferably from 0.1% to 20% by weight, and more preferably from 1% to 15% by weight relative to the total weight of the composition.

Oil

The composition according to the present invention may preferably include at least one oil.

The oil can be volatile or non-volatile. Preferably, the oil is a non-volatile oil.

The non-volatile hydrocarbon-based oil may be selected from:

hydrocarbon-based oils of animal origin, such as perhydrosqualene, hydrocarbon-based oils of plant origin, such as phytostearyl esters, such as phytostearyl oleate, phytostearyl isostearate and lauroyl/octyldodecyl/phytostearyl glutamate, triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cottonseed oil, coconut oil, marrow seed oil, wheatgerm oil, jojoba oil, lily oil, macadamia oil, corn oil, meadowfoam oil, monoi oil, hazelnut oil, apricot kernel oil, walnut oil, olive oil, evening primrose oil, palm oil, blackcurrant seed oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof, or alternatively caprylic/capric acid triglycerides, linear or branched hydrocarbons of mineral or synthetic origin, such as liquid paraffins and derivatives thereof, petroleum jelly, mineral oil, polydecenes, polybutenes, hydrogenated polyisobutene such as Parleam, and squalane;

synthetic ethers containing from 10 to 40 carbon atoms;

synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1$+$R_2$ 10. The esters may be chosen especially from fatty acid esters of alcohols, for example, cetyl esters, in particular, cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene 50 glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate fluoro oils that are optionally partially hydrocarbon-based and/or silicone-based, for instance fluorosilicone oils, fluoropolyethers and fluorosilicones;

fatty alcohols that are saturated or unsaturated, linear or branched, and contain 6 to 30 carbon atoms and more particularly from 8 to 30 carbon atoms: mention may be made of cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol; and mixtures thereof.

The oil may be present in a content ranging from 0.1% to 30% by weight, preferably from 0.5% to 20% by weight, and more preferably from 1% to 15% by weight relative to the total weight of the composition.

Aqueous Medium

The composition according to the present invention may preferably comprise an aqueous medium. The aqueous medium is made up of water or a mixture of water and at least one cosmetically acceptable solvent, preferably chosen from $C_1$-$C_4$ lower alcohols, such as ethanol, isopropanol, tert-butanol or n-butanol; polyols such as glycerin, propylene glycol and polyethylene glycols; and mixtures thereof.

The aqueous medium may be present in a content ranging from 20% to 99% by weight, preferably from 30% to 95% by weight, and more preferably from 40% to 90% by weight relative to the total weight of the composition.

pH Adjusters

The composition according to the present invention may preferably include at least one pH adjuster. The adjustment of the pH to the desired value may be carried out conventionally by addition of a pH adjuster, such as an organic or inorganic base or an organic or inorganic acid or salts thereof to the composition. The base includes, for example, ammonium hydroxide, sodium hydroxide, sodium carbonate or a primary, secondary or tertiary (poly) amine, such as monoethanolamine, diethanolamine, triethanolamine, isopropanolamine or 1, 3-propanediamine. The organic acid includes, for example, a carboxylic acid, a citric acid, and a lactic acid. The inorganic acid includes, for example, a hydrochloric acid, a nitric acid, orthophosphoric acid and a sulphonic acid. The salt includes, for example, sodium phosphate and trisodium phosphate.

The pH adjuster(s) may be present in a content sufficient to adjust the pH of the composition to the desired value, for example, ranging from 0.01% to 10% by weight, preferably from 0.1% to 5% by weight, and more preferably from 0.5% to 3% by weight relative to the total weight of the composition.

Additives

The compositions according to the present invention may further contain all the customary adjuvants encountered in the field of compositions for treating keratin fibers, for example, hydrophilic solvents, perfumes, fragrances, thickeners, preservatives such as chlorhexidine digluconate, sequestrants such as EDTA (ethylenediaminetetraacetic acid) and its salts, starch and derivatives thereof, such as potato starch esterified with halogenated methyl amino dipropionate acid (INCI name: POTATO STARCH MODIFIED), foam modifiers, colorants, moisturizing agents, antidandruff agents, antiseborrhoeic agents, sunscreens and the like.

The amount of the additives included in the composition according to the present invention is not limited, but may be from 0.01 to 30% by weight relative to the total weight of the composition according to the present invention.

The composition according to the present invention may exist in any form such as a lotion, a gel, a W/O or O/W emulsion, thickened or not, a foam, or a cream. The composition according to the present invention may be contained in any container such as a spray bottle, a pump bottle or an aerosol can.

The compositions according to the present invention can be used as compositions for treating keratin fibers. For example, the compositions can be formulated into shampoos, conditioners, hair treatment creams, gels, mousses, pump hair sprays, aerosol hair sprays, set lotions, blow styling lotions, hair color lotions, hair relaxing compositions, reducers for permanent wave, neutralizers for a permanent wave treatment, and coloring compositions.

Especially, since the composition according to the present invention possesses the superior effect of imparting smoothness to hair in consideration of an increased amount of silicone deposition on the surface of hair, the composition is suitable for hair care treatment compositions. Preferably, the composition according to the present invention can be a rinse-off type hair care treatment composition.

The pH of the composition according to the present invention may generally be, for example, from 2 to 12. When the composition is used as a hair care treatment composition, the composition may have a pH ranging from 3.0 to 6.0, and preferably from 3.5 to 5.0.

The viscosity of the composition according to the present invention is not particularly limited. Preferably, the viscosity of the composition according to the present invention ranges from 1 to 1,000,000 $mm^2/s$, more preferably from 2 $mm^2/s$ to 500,000 $mm^2/s$, and even more preferably from 5 $mm^2/s$ to 100,000 $mm^2/s$ at 25° C. The viscosity of the composition according to the present invention can be measured using a Poiseuille rheometer, at a temperature of 25° C., according to standard ASTM-D445-97.

A benefit of the composition according to the present invention having a low viscosity can be that the composition can be easily applied to keratin fibers, such as hair. For example, the composition having a viscosity less than 50 $mm^2/s$ can be applied to keratin fibers using a standard pump spray, such as a pump spray sold by Takemoto Packaging Inc. In addition, the composition having a viscosity less than 30 $mm^2/s$ can be applied to keratin fibers with a dipping method. Therefore, in one preferred embodiment of the present invention, the composition according to the present invention has a viscosity less than 50 $mm^2/s$, and more preferably less than 30 $mm^2/s$ at 25° C.

The composition according to the present invention can be manufactured through usual techniques in the art, for example, by mixing the (a) tartaric acid, the (b) aromatic alcohol, and the silicones of the (c) organopolysiloxane and the (d) amino-modified silicone. Said other ingredients can be mixed with the tartaric acid, the aromatic alcohol, and the silicones. While mixing these ingredients, they can be heated, if necessary.

[Cosmetic Process]

The present invention also relates to a process, preferably a cosmetic process for treating keratin fibers, preferably for conditioning or caring for hair, comprising a step of applying the composition according to the present invention to keratin fibers, preferably hair.

The composition may be applied to the hair by first applying to the hands, and then contacting the hair with the hands; in other embodiments, the composition may be applied directly onto the hair, such as by spraying. The composition may also be delivered onto the hair by use of an applicator or device, such as a brush. The composition, in particular the composition having a viscosity less than 30 $mm^2/s$, may also be applied to keratin fibers by dipping keratin fibers in the composition in a container. The compositions may be applied to the hair as a leave-on treatment or rinse-off treatment.

In one embodiment of the present invention, the composition can be used as a hair care or hair conditioning composition. Therefore, the present invention also relates to a use of the combination of the tartaric acid, the aromatic alcohol, the organopolysiloxane selected from polydialkylsiloxane, polydiarylsiloxane, and polyalkylarylsiloxane, and the amino-modified silicone as a hair care or hair conditioning composition.

In consideration of the superior effect of imparting smoothness to the hair of the composition according to the present invention, the cosmetic process according to the present invention can provide an attractive appearance and enhanced manageability to the hair over a long term.

Furthermore, thanks to the increased amount of silicone deposition on keratin fibers, the cosmetic process according to the present invention can impart long-lastingness of the cosmetic effects to keratin fibers.

EXAMPLES

The present invention will be described in a more detailed manner by way of examples. However, these examples should not be construed as limiting the scope of the present invention.

In the examples, the tartaric acid used was obtained from CRODA, the phenoxyethanol used was obtained from SEPPIC, the polydimethylsiloxane (dimethicone) used was obtained from SHINETSU, sold under the name "X-52-2127", and the amino-modified silicone (amodimethicone) used was obtained from DOW CORNING, sold under the name "DOW CORNING® 969 EMULSION". Shin-Etsu X-52-2127 comprises 75% polydimethylsiloxane and Dow Corning 969 Emulsion comprises 30% of amodimethicone.

Examples 1 and 2 and Comparative Example 1

[Composition]

The compositions according to Examples 1 and 2 and Comparative Example 1 was prepared in accordance with the following preparation protocol. The compositions are shown in Table 1 below. In Table 1, all components are based on "% by weight" as active raw materials.

[Preparation Protocol]
1) Glycerin, cetyl esters, mineral oil, stearyl alcohol, and tartaric acid, if present, were added to deionized water at 80° C. in a beaker and mixed.
2) Behentrimonium chloride was added to obtain an emulsified mixture, then the mixture was cooled to about 45° C.
3) Dimethicone and amino-modified silicone (amodimethicone) were added to the mixture.
4) Phenoxyethanol, and fragrance were added to the mixture.
5) The pH of the obtained mixture was adjusted to 4.0 with sodium hydroxide.
6) The total amount was adjusted with deionized water. The obtained mixture was mixed so as to be homogenous.

[Evaluation 1]
(Measurement of Silicone Deposition)

3 hair swatches (1 g, 27 cm) were prepared for each experiment. Each of the swatches was washed with clarifying shampoo and then placed on a hot plate at 30° C. 0.4 g of each of the compositions according to Examples 1 and 2 and Comparative Example 1 was applied on each swatch with a brush. The hair swatch was then wrapped and kept at 30° C. and ambient humidity for 5 minutes, rinsed off under running water, and then dried naturally under ambient conditions to obtain the treated hair swatch. The treated swatch was cut into short pieces for measurement. The amount of silicone deposited on the swatch was measured with X-ray fluorescence analysis (XRF) using a wavelength dispersive X-ray fluorescence spectrometer (Manufacturer: Thermo Fisher Scientific K.K., Model: WDXRF ARL Optim'x Thermofisher 2104 (Wavelength Dispersion) XRF system). The average values were calculated with 3 hair swatches for each composition.

(Smoothness)

3 hair swatches (1 g, 27 cm) were prepared for each experiment. The hair swatches were washed with clarifying shampoo and then placed on a hot plate at 30° C. 0.4 g of each of the compositions according to Examples 1 and 2 and Comparative Example 1 was applied on the swatch with a brush. The hair swatch was then wrapped and kept at 30° C. and ambient humidity for 5 minutes, rinsed off under running water, and then dried naturally under ambient conditions to obtain the treated hair swatch. The treated hair swatch was placed on a plate, and its root side was fixed on the plate with a hair clip. The smoothness of the treated hair swatch was evaluated by scanning the swatch from root to tip with a sensor (Handy Rub Tester (type TL701) from Trinity Lab) and measuring COF (Coefficient of Friction). The measurement was carried out 3 times for one treated hair swatch. The same procedure was conducted with two more hair swatches to obtain 9 results in total for one composition, and the mean values were calculated for each composition. A lower score indicates that a better smoothness effect was exerted.

The results are shown in Table 1.

TABLE 1

| Ingredients | Ex. 1 | Ex. 2 | Comp. Ex. 1 |
| --- | --- | --- | --- |
| Glycerin | 2 | 2 | 2 |
| Behentrimonium Chloride | 3.8 | 3.8 | 3.8 |
| Mineral Oil | 0.5 | 0.5 | 0.5 |
| Cetyl Esters | 1 | 1 | 1 |
| Stearyl Alcohol | 8 | 8 | 8 |
| Dimethicone | 8 | 8 | 8 |
| Amodimethicone | 4.84 | 4.84 | 4.84 |
| Phenoxyethanol | 1 | 1 | 1 |
| Tartaric Acid | 0.5 | 1 | — |
| Fragrance | 0.7 | 0.7 | 0.7 |
| Sodium Hydroxide | qs pH 4.0 | qs pH 4.0 | qs pH 4.0 |
| Deionized Water | qs 100 | qs 100 | qs 100 |
| Evaluation | | | |
| Average Silicone Deposition (ppm) | 3351 | 3442 | 1774 |
| Smoothness (COF) | 0.032 | 0.035 | 0.044 |

As can be seen from the results of the measurement of amounts of silicone deposition on the hair swatches in Table 1, the compositions according to Examples 1 and 2, which comprise tartaric acid in an amount of 0.3% by weight or more relative to the total weight of the composition, aromatic alcohol, organopolysiloxane selected from polydialkylsiloxane, polydiarylsiloxane, and polyalkylarylsiloxane, and amino-modified silicone, provided more silicone deposition on the hair swatch and exhibited a better smoothness effect compared to the compositions according to Comparative Example 1, which does not comprise tartaric acid.

[Evaluation 2]

Long-lastingness of silicone deposition was evaluated using the hair swatches treated with the composition according to Examples 1 and 2 and Comparative Example 1 above as the sample. The hair swatch was washed with a shampoo composition a predetermined number of times. The washed swatch was cut into short pieces for measurement. The amount of silicone deposited on the swatch after shampooing was measured with X-ray fluorescence analysis (XRF) using a wavelength dispersive X-ray fluorescence spectrometer (Manufacturer: Thermo Fisher Scientific K.K., Model: WDXRF ARL Optim'x Thermofisher 2104 (Wavelength Dispersion) XRF system). The compositions of the shampoo composition are shown in Table 2 below. In Table 2, all components are based on "% by weight" as active raw materials.

TABLE 2

| Ingredients | % by weight |
| --- | --- |
| Hexylene Glycol | 1 |
| Sodium Chloride | 1 |
| Coco-betaine | 9 |
| Polyquaternium-10 | 0.3 |
| Sodium Benzoate | 0.5 |
| Salicylic Acid | 0.2 |
| Citric Acid | qs pH 5.3 |
| Sodium Hydroxide | qs pH 5.3 |
| Deionized Water | qs 100 |

The results are shown in Table 3.

TABLE 3

| | Number of Shampooings | Ex. 1 | Ex. 2 | Comp. Ex. 1 |
| --- | --- | --- | --- | --- |
| Average Silicone Deposition (ppm) | 0 | 3351 | 3442 | 1774 |
| | 3 | 1874 | 2561 | 649 |
| | 5 | 945 | 1949 | 319 |

As can be seen from the results of the measurements of amounts of silicone deposition on the hair swatch, the hair swatches treated with each of the compositions according to Examples 1 and 2 maintained about 0.56 and about 0.74 times the initial silicone deposition level even after they were shampooed 3 times, and maintained about 0.28 and about 0.57 times the initial silicone deposition level even after they were shampooed 5 times, respectively. On the other hand, the hair swatches treated with the compositions according to Comparative Example 1 maintained only about 0.37 and about 0.18 times the initial silicone deposition level after they were shampooed 3 and 5 times, respectively. This result also indicates that the more concentration of tartaric acid provides a greater amount of silicone deposition remaining on hair after shampooing.

Accordingly, it can be said that the composition according to the present invention can impart improved long-lastingness of the cosmetic effects to keratin fibers, such as hair, produced from the silicone deposition. In particular, since a difference of even 100 ppm of the silicone deposition on hair can be tangible by, for example, touching the hair, the improvement of smoothness of hair and its long-lastingness according to the present invention is remarkable.

Therefore, it can be concluded that the composition according to the present invention is very preferable for use to increase the amount of silicone deposition on keratin fibers, such as hair, to achieve improved cosmetic effects, such as hair smoothness and enhanced manageability of hair, as well as long-lastingness of the cosmetic effects.

Example 3 and Comparative Example 2

[Composition]

The emulsion compositions according to Example 3 and Comparative Example 2 were prepared in accordance with the following preparation protocol. The formulation is shown in Table 4 below. In Table 4, all components are based on "% by weight" as active raw materials.

TABLE 4

| Ingredients | Ex. 3 | Comp. Ex. 2 |
| --- | --- | --- |
| Polysorbate 20 | 0.3 | 0.3 |
| Behentrimonium Chloride | 1 | 1 |
| Quaternium-87 | 1 | 1 |
| Potato Starch Modified | 1.25 | 1.25 |
| Cetyl Esters | 1 | 1 |
| Stearyl Alcohol | 3 | 3 |
| Dimethicone | 2.4 | 2.4 |
| Amodimethicone | 1.45 | 1.45 |
| Phenoxyethanol | 0.9 | — |
| Tartaric Acid | 1 | — |
| Fragrance | 0.4 | 0.4 |
| Sodium Hydroxide | qs pH 4.0 | qs pH 4.0 |
| Deionized Water | qs 100 | qs 100 |

[Preparation Protocol]

1) Polysorbate 20, cetyl esters, potato starch modified, stearyl alcohol, and tartaric acid, if present, were added to deionized water at 80° C. in a beaker and mixed.

2) Behentrimonium chloride and Quaternium-87 was added to obtain an emulsified mixture, then the mixture was cooled to about 45° C.

3) Dimethicone and amodimethicone were added to the mixture.

4) Phenoxyethanol, if present, and fragrance were added to the mixture.

5) The pH of the obtained mixture was adjusted to 4.0 with sodium hydroxide.

6) The total amount was adjusted with deionized water. The obtained mixture was mixed so as to be homogenous.

[Evaluation 3]

(Viscosity)

Each of the viscosities of the compositions according to Example 3 and Comparative Examples 2 was measured using a Poiseuille rheometer, at a temperature of 25° C., according to standard ASTM-D445-9.

(Smoothness)

3 hair swatches (1 g, 27 cm) were prepared for each experiment. The hair swatches were washed with clarifying shampoo and then placed on a hot plate at 30° C. 0.4 g of each of the compositions according to Example 3 and Comparative Example 2 was applied on the swatch with a brush. The hair swatch was then wrapped and kept at 30° C. and ambient humidity for 5 minutes, rinsed off under running water, and then dried naturally under ambient conditions to obtain the treated hair swatch. The treated hair swatch was placed on a plate, and its root side was fixed on the plate with a hair clip. The smoothness of the treated hair swatch was evaluated by scanning the swatch from root to tip with a sensor (Handy Rub Tester (type TL701) from Trinity Lab) and measuring COF (Coefficient of Friction). The measurement was carried out 3 times for one treated hair swatch. The same procedure was conducted with two more hair swatches to obtain 9 results in total for one composition, and the mean values were calculated for each composition. A lower score indicates that a better smoothness effect was exerted. The sample "Ref" in Table 5 is a result measured to untreated hair swatch without allocation of any products.

The results of these tests are shown in Table 5.

TABLE 5

|  | Ex. 3 | Comp. Ex. 2 | Ref |
| --- | --- | --- | --- |
| Viscosity (mm²/s) | 33 | 55 | — |
| Smoothness (COF) | 0.100 | 0.119 | 0.218 |

As can be seen from the results of the measurement of smoothness in Table 5, the compositions according to Example 3, which comprise tartaric acid in an amount of 0.3% by weight or more relative to the total weight of the composition, aromatic alcohol, organopolysiloxane selected from polydialkylsiloxane, polydiarylsiloxane, and polyalkylarylsiloxane, and amino-modified silicone, exhibited a better smoothness effect compared to the compositions according to Comparative Example 2, which does not comprise tartaric acid and aromatic alcohol, even if the composition has a very low viscosity.

(Dipping Test)

The purpose of this experimental example is to show a benefit of the composition according to the present invention having a low viscosity. This experimental example does not intend to limit the scope of the present invention in light of viscosity.

In a bowl of opening 15 centimeters, 25 g of each of the compositions according to Example 3 and a traditional creamy conditioner with a much higher viscosity of greater than 60 mm²/s was placed. A hair swatch (100 g, 27 cm) was lowered into the bowl containing the liquid. The hair swatch can descend easily into the composition according to Example 3 without being pushed, or otherwise forced. After a few seconds the hair can be removed from the bowl and more than 90% by weight of the composition according to Example 3 was attached to the hair. On the other hand, the hair swatch did not penetrate into the traditional creamy conditioner and more than 90% by weigh of the traditional creamy conditioner remained in the bowl after the hair swatch was removed.

This result of the dipping test demonstrated that the composition according to the present invention having a low viscosity can be easily applied to the hair by dipping compared to traditional compositions having a high viscosity. Therefore, it can be said that the low-viscosity composition according to the present invention has a benefit that it can be easily applied to keratin fibers, such as hair.

The invention claimed is:

1. A composition for treating keratin fibers comprising:
   (a) tartaric acid in an amount of 0.3% by weight or more, relative to the total weight of the composition,
   (b) at least one aromatic alcohol in an amount of 0.5% by weight or more relative to the total amount of the composition,
   (c) at least one organopolysiloxane chosen from polydialkylsiloxane, polydiarylsiloxane, or polyalkylarylsiloxane, and
   (d) at least one amino-modified silicone, wherein the aromatic alcohol is represented by general formula (I):

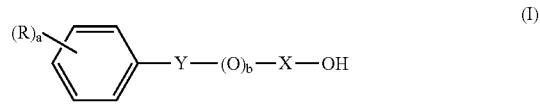

(I)

wherein,
a is an integer chosen from 0 or 1;
b is an integer of 1;
R is H, a halogen, or a C1 to C6 alkyl group;
X is a $C_1$ to $C_4$ alkylene group; and
Y is a single bond.

2. The composition according to claim 1, wherein in formula (I), a is 0.

3. The composition according to claim 1, wherein the aromatic alcohol is phenoxyethanol.

4. The composition according to claim 1, wherein the organopolysiloxane is selected from a polydialkylsiloxane.

5. The composition according to claim 1, wherein the organopolysiloxane is polydimethylsiloxane.

6. The composition according to claim 1, wherein the tartaric acid is present in an amount ranging from 0.3% to about 20% by weight, relative to the total weight of the composition.

7. The composition according to claim 1, wherein the tartaric acid is present in an amount ranging from about 0.5% to about 10% by weight, relative to the total weight of the composition.

8. The composition according to claim 1, wherein the aromatic alcohol is present in an amount ranging from 0.5% to about 10% by weight, relative to the total weight of the composition.

9. The composition according to claim 1, wherein the aromatic alcohol is present in an amount ranging from 0.5% to about 3% by weight, relative to the total weight of the composition.

10. The composition according to claim 1, wherein the organopolysiloxane is present in an amount ranging from about 0.1% to about 30% by weight, relative to the total weight of the composition.

11. The composition according to claim 1, wherein the organopolysiloxane is present in an amount ranging from about 2% to about 15% by weight, relative to the total weight of the composition.

12. The composition according to claim 1, wherein the amino-modified silicone is present in an amount ranging from about 0.1% to about 20% by weight, relative to the total weight of the composition.

13. The composition according to claim 1, wherein the amino-modified silicone is present in an amount ranging from about 1% to about 10% by weight, relative to the total weight of the composition.

14. The composition according to claim 1, further comprising at least one surfactant chosen from cationic, anionic, nonionic, or amphoteric surfactants.

15. The composition according to claim 1, further comprising at least one oil.

16. The composition according to claim 1, wherein the composition is a rinse-off cosmetic composition.

17. A cosmetic process for caring for or conditioning keratin fibers comprising: applying onto the keratin fibers the composition of claim 1.

* * * * *